United States Patent [19]

Fujiyama et al.

[11] 3,988,424
[45] Oct. 26, 1976

[54] METHOD FOR DECOMPOSING AN AROMATIC ALDEHYDE-HYDROGEN FLUORIDE-BORON TRIFLUORIDE COMPLEX

[75] Inventors: Susumu Fujiyama; Takehiko Takahashi; Minoru Takagawa; Shigeki Ozao, all of Niigata, Japan

[73] Assignee: Mitsubishi Gas Chemical Company, Inc., Tokyo, Japan

[22] Filed: Dec. 11, 1975

[21] Appl. No.: 639,698

[30] Foreign Application Priority Data
Dec. 27, 1974 Japan.............................. 49-148840

[52] U.S. Cl................................ 423/293; 260/599; 260/683.48; 423/483
[51] Int. Cl.².................... C07C 45/14; C01B 35/06
[58] Field of Search ............ 423/283, 483; 260/599, 260/671, 683.48, 683.44

[56] References Cited
UNITED STATES PATENTS

| | | | |
|---|---|---|---|
| 2,430,516 | 11/1947 | Lien et al........................ | 423/483 X |
| 3,284,508 | 11/1966 | Gray et al............................ | 260/599 |
| 3,948,998 | 4/1976 | Fujiyama et al.................... | 260/599 |

FOREIGN PATENTS OR APPLICATIONS
713,335   8/1954   United Kingdom

Primary Examiner—G. O. Peters
Attorney, Agent, or Firm—Flynn & Frishauf

[57] ABSTRACT

A method for decomposing an aromatic aldehyde-hydrogen fluoride-boron trifluoride complex in the presence of a decomposing agent represented by the formula

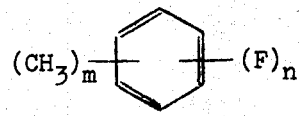

wherein $n$ is integer of 1–6, inclusive, and $m$ is integer of 0–5, inclusive, and a total of $n$ and $m$ is 6 or less, to obtain an aromatic aldehyde, hydrogen fluoride and boron trifluoride separately without causing any change in the quality of the aromatic aldehyde or without forming undesirable byproducts is disclosed.

7 Claims, 2 Drawing Figures

METHOD FOR DECOMPOSING AN AROMATIC ALDEHYDE-HYDROGEN FLUORIDE-BORON TRIFLUORIDE COMPLEX

BACKGROUND OF THE INVENTION

This invention relates to a process for decomposing an aromatic aldehyde-hydrogen fluoride-boron trifluoride complex in the presence of a specific decomposing agent, whereby the aromatic aldehyde, hydrogen fluoride and boron trifluoride can be obtained separately, and particularly relates to a process for heat-decomposing an aromatic aldehyde-hydrogen fluoride-boron trifluoride complex without causing any change in the quality of the aromatic aldehyde.

It has been known that p-tolualdehyde can be prepared in a high yield and with a high selectivity with a small amount of o-tolualdehyde as a byproduct by reacting toluene with carbon monoxide by using a catalyst consisting of hydrogen fluoride and boron trifluoride. The reaction is one of the two reactions that constitute the process for producing terephthalic acid from toluene; and p-tolualdehyde obtained through the reaction is used as a starting material for organic synthesis of per-p-toluic acid and p-cresol, etc. and for preparation of polymers. Similarly, 2,4-dimethyl benzaldehyde and 2,4,5,-trimethyl benzaldehyde are formed by reacting m-xylene with carbon monoxide and by reacting pseudocumene with carbon monoxide, respectively.

An aromatic aldehyde-hydrogen fluoride-boron trifluoride complex is formed through the above reaction. In attempting to decompose the complex to obtain an aromatic aldehyde, hydrogen fluoride and boron trifluoride separately, a change in quality of the aromatic aldehyde usually occurs in the presence of the hydrogen fluoride and boron trifluordie, because of the strong bonding force between the aromatic aldehyde and the catalyst. The change in quality of the aldehyde in the decomposing column means the loss of the aromatic aldehyde itself. Furthermore, a small amount of water is produced as a result of the reaction causing the change in quality of the aromatic aldehyde. Water so produced not only deactivates some of the catalysts, but also corrodes the apparatus used for carrying out the reaction. It is necessary to avoid any change in quality of the aromatic aldehyde in case of separating the aromatic aldehyde from the complex. Therefore, the production of water should be kept as low as possible, and it is necessary to decompose the aromatic aldehyde-hydrogen fluoride-boron trifluoride complex as rapidly as possible. Also, it is important to select a deomposing column for effectively carrying out gas-liquid contact. It is preferable to contact the complex with the vapour of a decomposing agent by introducing the complex into the column while refluxing the decomposing agent therein.

For example, British Pat. No. 713,335 discloses a method for continuously obtaining hydrogen fluoride, boron trifluoride and an aromatic aldehyde separately by heat-decomposing an aromatic aldehyde-hydrogen fluoride-boron trifluoride complex, while refluxing a diluent selected from the group consisting of toluene and chlorobenzene in the decomposition system. However, this method has the following disadvantages: (a) The undecomposed boron trifluoride in the form of complex remains in the separated aromatic aldehyde, and (b) the reaction vessel must be made of silver, which is expensive, to prevent corrosion of the vessel by the water which is produced as a result of the reaction causing the change in quality of the aromatic aldehyde. Though it is commercially preferable that such decomposition be conducted under superpressure, a particularly striking loss of the aromatic aldehyde results by maintaining the aromatic aldehyde-hydrogen fluoride-boron trifluoride complex under superpressure. Therefore, since the method of the British Patent has these disadvantages, it can not be said to be a suitable one.

In the U.S. Pat. No. 2,534,017 by Gresham et al, a two-step process for decomposing a p-tolualdehyde-hydrogen fluoride-boron trifluoride complex is disclosed. In the Gresham Patent the first step is effected at a reduced pressure in the absence of any diluent. In the Gresham et al, toluene and cetane are used as a diluent.

In the application of Fujiyama et al, Ser. No. 468025 fled May 8, 1974, now U.S. Patent No. 3,962,343, benzene is used as a diluent for decomposing an aromatic aldehyde-hydrogen fluoride-boron trifluoride complex.

SUMMARY OF THE INVENTION

The inventors of the present invention have carried out research on the relationship between the kind of decomposing agents for decomposing an aromatic aldehyde-hydrogen fluoride-boron trifluoride complex and the amount of change in quality of the aromatic aldehyde. As a result, it was found that the kind of decomposing agent has a great influence upon the degree of change in quality of the aldehyde. It was also found that the reaction causing the change in quality of the aromatic aldehyde is probably the condensation reaction of the aromatic aldehyde with a decomposing agent or with unreacted aromatic hydrocarbon to form for example, triarylmethane, and that undesirable water is produced through the condensation reaction.

The reaction causing the change in quality of the aromatic aldehyde is accelerated by using a large amount of hydrogen fluoride and boron trifluoride, by effecting decomposition of the complex at an elevated temperature, or by effecting decomposition of the complex for a long period. In particular, the more hydrogen fluoride there is in the decomposing system, the greater the rate of the reaction causing the change in quality of the aromatic aldehyde. This is because the amounts of hydrogen fluoride and boron trifluoride present in the decomposing system have a great influence upon the temperature at which the reaction occurs. For example, when there is an excess amount of hydrogen fluoride in the column, the reaction is effected at a temperature below room temperature. On the other hand, when boron trifluoride alone is present in the system, or when a small amount of hydrogen fluoride besides boron trifluoride is present in the system, the rate of the reaction causing the change in quality of the aromatic aldehyde is slow even at an elevated temperature. When materials other than hydrogen fluoride and boron trifluoride are present in the system, the materials generally accelerate or suppress the reaction. It is necessary that a decomposing agent for decomposing the aromatic aldehyde-hydrogen fluoride-boron trifluoride complex be inert to the aromatic aldehyde. It is also necessary that the decomposing agent suppress to a considerable extent any reaction causing any chage in quality of the aromatic aldehyde. We have found that a fluorine-nuclear substituted aromatic aldehyde represented by the formula

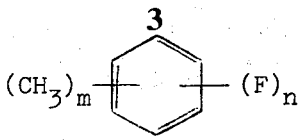

where *n* is integer of from 1 to 6, inclusive, and *m* is integer of from 0 to 5, inclusive, and a total of *n* and *m* is 6 or less satisfies the above requirements as a decomposing agent. In other words, we have found that little change in quality of the aromatic aldehyde occurs, when the aromatic aldehyde-hydrogen fluoride-boron trifluoride complex is decomposed in the presence of the fluorine-nuclear substituted aromatic hydrocarbon.

Therefore, it is an object of this invention to provide a commercially usable process for continuously obtaining an aromatic aldehyde, hydrogen fluoride and boron trifluoride separately in a high yield or in a high recovery ratio by decomposing an aromatic aldehyde-hydrogen fluoride-boron trifluoride complex in the presence of a specific decomposing agent.

Another object of this invention is to provide a process for obtaining an aromatic aldehyde, hydrogen fluoride and boron trifluoride separately from an aromatic aldehyde-hydrogen fluoride-boron trifluoride complex without causing any change in the quality of the aromatic aldehyde.

Other objects of the invention will in part be obvious and will in part appear hereinafter.

BRIEF DESCRIPTION OF THE INVENTION

DETAILED DESCRIPTION OF THE INVENTION

This invention relates to a process for decomposing an aromatic aldehyde-hydrogen fluoride-boron trifluoride complex to obtain an aromatic aldehyde, hydrogen fluoride and boron trifluoride separately, characterized by carrying out the decomposition in the presence of a decomposing agent represented by the formula

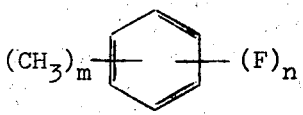

wherein *n* is integer of 1–6, inclusive, and *m* is integer of 0–5, inclusive, and a total of *n* and *m* is 6 or less.

Figure 2:
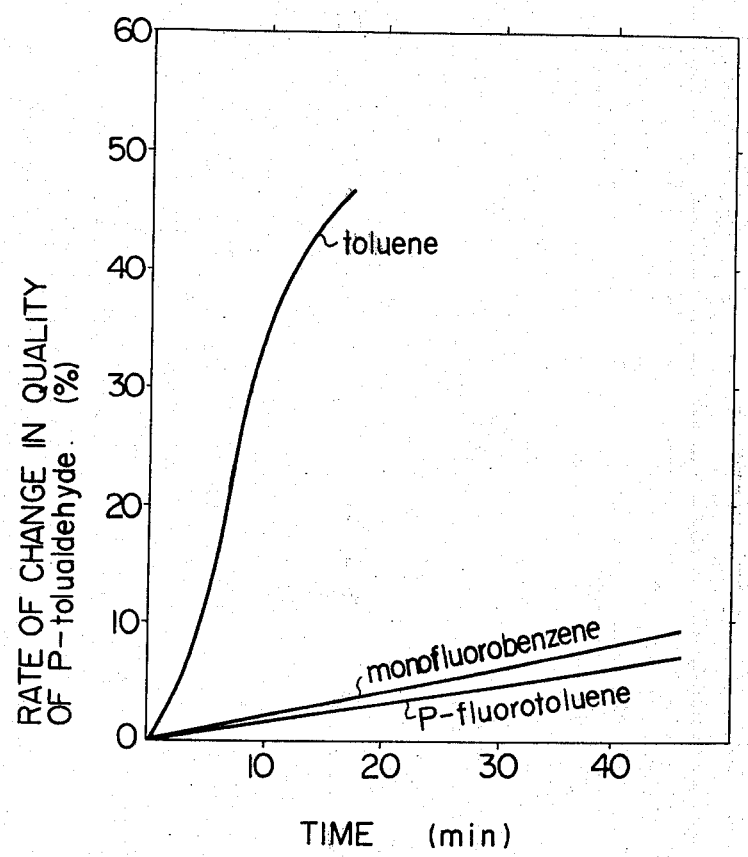
FIG. 2 is a graph showing the relationship between the degree of the change in quality of the aromatic aldehyde and the kind of decmposing agents, such as monofluoro-benzene, p-fluorotoluene and toluene in case of decomposing an aromatic aldehyde-hydrogen fluoride-boron trifluoride complex in the presence of said decomposing agent.

Into the vessel were introduced 1 mol of p-tolualdehyde, 1.7 mol of hydrogen fluoride, 0.9 mol of boron trifluoride and 11 mol of monofluorobenzene. The temperature in the vessel was maintained at 120° C, and change in the formation of byproduct with time was determined. The above procedures were repeated using p-fluorotoluene and toluene. The results are shown in FIG. 2 and make clear that monofluorobenzene and p-fluorotoluene are more effective in suppressing to a considerable extent the change in quality of the aromatic aldehyde than toluene.

Typical examples of the decomposing agents include mono-, di-, tri-, tetra-, penta- and hexa-fluorobenzenes; o-, m- and p-fluorotoluenes; di-, tri-, tetra-, pentafluorotoluenes, and mono-, di-, tri- and tetra-fluoroxylenes. Fluorobenzenes and mono-fluorotoluenes are preferred as the decomposing agents of this invention, and monofluorobenzene and p-fluorotoluene are most preferred. This is because fluorobenzenes and monofluorotoluenes are stable in the presence of hydrogen fluoride and boron trifluoride. One of the above mentioned decomposing agents or mixtures thereof can be used in the present invention.

The decomposition of the aromatic aldehyde-hydrogen fluoride-boron trifluoride complex in the presence of the decomposing agent is conveniently carried out at a temperature within the range of from 100° C to 200° C. Hydrogen fluoride can be dissociated from the complex at a low temperature, but generally boron trifluoride is difficult to be dissociated from an aromatic aldehyde-boron trifluoride complex at a temperature below than 100° C. Also, the change in quality of the aromatic aldehyde tends to be accelerated at a temperature more than 200° C. In general, the decomposing temperaure may be determined by the boiling point of the decomposing agent which is refluxed in the decomposing system. In other words, the decomposing temperature depends on the kind of the decomposing agent and the decomposing pressure. For example, in case of using monofluorobenzene as the decomposing agent, and of using each of 2, 4 and 6 atmospheres absolute (ata) of the decomposing pressure, the main portion of the decomposing column is maintained at a temperature corresponding to the boiling point of monofluorobenzene under the predetermined decomposing pressure, that is, the main portion of the decomposing column is maintained at a temperature of 110°, 140° and 160° C corresponding to the boiling point of monofluorobenzene under the decomposing pressure of 2, 4 and 6 ata, respectively. In other words the decomposition is carried out at the temperature mentioned above. But the top portion of the decomposing column is maintained at a temperature lower than the above temperature, because the partial pressure of each of hydrogen fluoride and boron trifluoride at the top portion of the column is higher than the partial pressure of each of hydrogen fluoride and boron trifluoride at the intermediate portion of the column, and similarly, the bottom portion of the column at which the aromatic aldehyde is condensed is maintained at a temperature higher than the above temperature.

It is advantageous that the decomposition be carried out at a relatively low pressure. However, it is preferable that the decomposing pressure be higher than one atmospheric pressure to insure that the catalyst consisting of hydrogen fluoride and boron trifluoride is recycled into the reaction system in which an aromatic hydrocarbon reacts with carbon monoxide. Therefore, considering the above facts, the decomposition is conveniently carried out at a pressure within the range of from 2 ata to 6 ata. In the decomposing pressure as mentioned above, boron trifluoride in a gaseous state decomposed in the column can be recycled into the reaction system in which an aromatic hydrocarbon reacts with carbon monoxide for reusing it without compressing it, so the decomposing pressure in the range as mentioned above is preferred from an economical point of view.

It is preferable to reflux sufficient amount of the decomposing agent in the decomposing system for effectively carrying out the decomposition of the complex. The amount of the decomposing agent refluxed in the system may range between 15 and 40 mol per 1 mol of the aromatic aldehyde supplied as the synthetic solution into the decomposing column. Refluxing too little decomposing agent in the system retards the rate of supplying the heat necessary to decompose the aromatic aldehyde-hydrogen fluoride-boron trifluoride complex. Refluxing too much of the decomposing agent is not economical.

Figure 1:
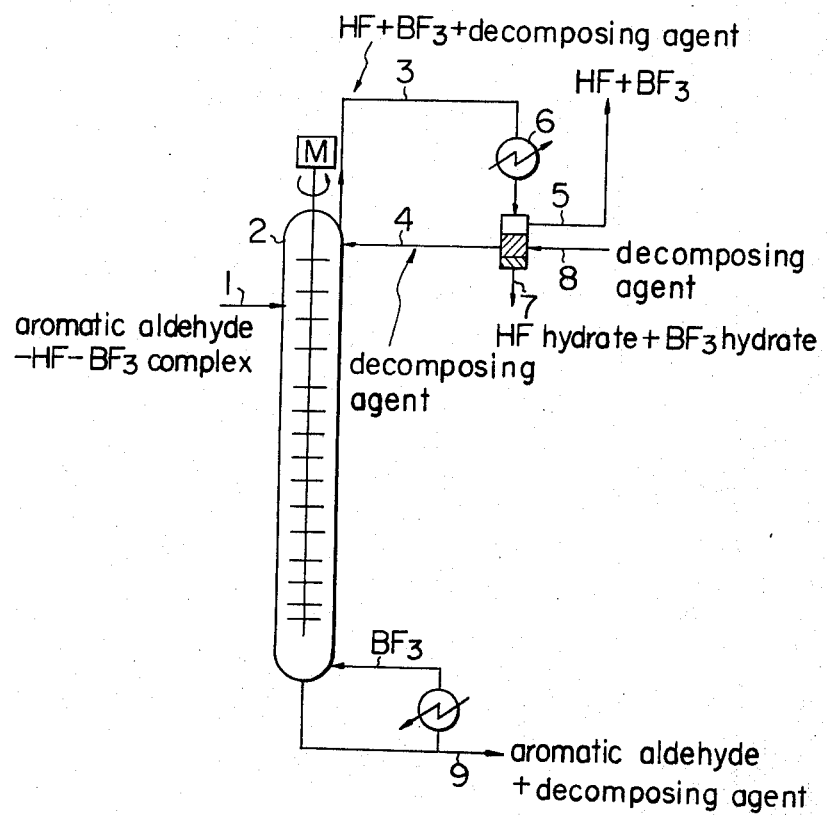
FIG. 1 is a flow sheet for showing a series of treatments.

This invention is illustrated by the following non-limitative FIG. 1.

The synthetic solution of the aromatic aldehyde-hydrogen fluoride-boron trifluoride complex to be decomposed is generally introduced into the portion near the top of decomposing column 2 through line 1. The decomposing agent, such as monofluorobenzene or monofluorotoluenes, is refluxed in the decomposing system. While the synthetic solution is diluted by the decomposing agent and flows down through the column, hydrogen fluoride and boron trifluoride are dissociated from the complex.

The mixture of the aromatic aldehyde and major part of the decomposing agent is drained off from column 2 through line 9. After the very small amount of boron trifluoride contained therein is removed from said mixture by washing with water, the mixture is fed into a distilling column (not shown) where the decomposing agent, toluene and a vary small amount of a high boiling point material are removed from the aromatic aldehyde. Fresh decomposing agent is fed into separator through line 8 to compensate for the amount of decomposing agent withdrawn through line 9.

Hydrogen fluoride, boron trifluoride and the minor part of decomposing agent are withdrawn from the top of column 2 through line 3, and are introduced to partial condenser 6, in which hydrogen fluoride, boron trifluoride and decomposing agent are cooled to the temperature at which the decomposing agent is condensed. The decomposing agent so condensed is refluxed to column 2 through line 4. Hydrogen fluoride and boron trifluoride are recovered through line 5, are condensed by cooling, and then are recycled to the reaction system for synthesis of the aromatic aldehyde through a suitable means (not shown) for reuse as a catalyst for the synthesis.

The catalyst which was deactivated by a very small amount of water is drained off through line 7. The deactivated catalyst is a mixture of hydrogen fluoride hydrate and boron trifluoride hydrate. These hydrates are regenerated by any of a variety of well-known means to hydrogen fluoride and boron trifluoride anhydride which are reused as a catalyst for synthesis of the aromatic aldehyde. When the aromatic aldehyde hydrogen fluoride-boron trifluoride complex is decomposed, a decomposing agent having a boiling point below 180° C is preferably used so as to easily carry out the distillation of the aromatic aldehyde.

Some of the decomposing agent is removed together with the dissociated aromatic aldehyde and some is entrained with hydrogen fluoride and boron trifluoride from the decomposing column, so supply of fresh decomposing agent to the decomposing column is constantly required to compensate for the output of the decomposing agent.

In the present invention, most of the hydrogen fluoride containing a small amount of boron trifluoride may be dissociated from the aromatic aldehyde-hydrogen fluoride-boron trifluoride complex in the upper portion of a decomposing column, followed by dissociating most of boron trifluoride containing a small amount of hydrogen fluoride in the lower portion thereof. In the above case, the decomposing agent is not necessarily requied in the lower portion in order to avoid change in quality of the aromatic aldehyde, because boron trifluoride contributes very little to the reaction causing the change in quality of the aromatic aldehyde. However, the decomposing agent and other solvents may be present in the lower portion as a diluent.

Alternatively, most of the hydrogen fluoride containing a small amount of boron trifluoride may be dissociated from the aromatic aldehyde-hydrogen fluoride-boron trifluoride complex in a first decomposing column, followed by dissociating most of boron trifluoride containing a small amount of hydrogen fluoride in a second decomposing column. In the above case, the decomposing agent is not necessarily required in the latter decomposing column, either. However, the decomposing agent and other solvent may be present in the second decomposing column as a diluent.

A gas-liquid contacting apparatus having a good efficiency and structure so as to shorten the holdup of liquid is desirable in order to lessen the change in quality of the aromatic aldehyde. Examples of decomposing columns suitable for carrying out the decomposition include a rapid gas-liquid contacting column, a spray column, a cascade tray, a column of film-evaporator type, a plate column having a few plates and an empty column. A column of film-evaporator type is preferred.

Preferably, the fluorine-nuclear substituted aromatic hydrocarbons used as the decomposing agent in the present invention do not bond strongly to hydrogen fluoride and boron trifluoride, and are stable therein. The decomposing agents of the present invention do not react with the aromatic aldehyde, and suppress to a considerable extent the reaction of the aromatic aldehyde with aromatic hydrocarbon such as toluene which was fed as an unreacted material from the system for synthesizing the aromatic aldehyde into the decomposing system, and do not corrode the apparatus. Furthermore, this invention has the following advantages: (a) The change in quality of aromatic aldehyde is very low, since the decomposition is effected in the presence of a specific decomposing agent; (b) hydrogen fluoride, boron trifluoride and the aromatic aldehyde are each obtained with maximum yield; and (c) the columns for carrying out the present process do not have to be made from an expensive corrosion-resistant material, e.g. silver. The present process is commercially usable, so the significance of this invention for industry is great.

The invention is further illustrated, but in no way limited, by the following Examples.

EXAMPLES 1 – 4 AND COMPARATIVE EXAMPLES 1 – 3

The decomposing column employed is made of stainless steel and has a length of 2500 mm and an inside diameter of 85 mm. Eight countercurrent perforated plates having the ratio of aperture of 20% and a size of aperture of 3 mm were arranged at regular intervals in the upper portion within a distance 500 mm from the top of the column, and a Dixon packing of 6 mm was placed in the under portion below a distance of 2000 mm from the bottom thereof. A first partial condenser for condensing the decomposing agent and a second partial condenser for condensing hydrogen fluoride were positioned above the top of the column. The first condenser was operated at a temperature so as not to condense hydrogen fluoride. The separator separating hydrogen fluoride and boron trifluoride from the decomposing agent was connected to the first condensor. Hydrogen fluoride and boron trifluoride were all withdrawn from the top of the column, and substantially all the decomposing agent employed was refluxed in the composing system. A reboiler was connected to the bottom of the column, and necessary heat was supplied therefrom.

Each of the synthetic solutions as shown in Table 1 from the reaction system of an aromatic hydrocarbon with carbon monoxide; and each of the decomposing agents as shown in Table 1 was continuously supplied into the second plate from the top of the column. The object product in the synthetic solution is p-tolualdehyde or 2,4-dimethyl-benzaldehyde obtained from toluene or m-xylene in the presence of hydrogen fluoride and boron trifluoride as a catalyst, respectively. The decomposing agent was monoflurorbenzene or p-fluorotoluene. A 30 – 40% by weight solution of the aromatic aldehyde in the decomposing agent was withdrawn from the bottom of the column. Low boiling point material, such as the decomposing agent, and high boiling point material produced by the change in quality of the aromatic aldehyde were separated from the withdrawal by distilling it, thereby recovering the object product, namely the aromatic aldehyde. The amount of the decomposing agent refluxed in the system was adjusted by the heat supplied from the reboiler. The pressure in the column was kept constant by adjusting the amount of gas withdrawn from the top of the column, whereby the temperature in the column was also kept constant.

The decomposing results are given in Table 1.

For comparison, the above processes were repeated except that toluene or monochlorobenzene was used as a decomposing agent. The results are given in Table 1 as Comparative Examples 1 – 3.

Table 1

| | Object product | Example 1 p-tolu-aldehyde | Example 2 p-tolu-aldehyde |
|---|---|---|---|
| contents of synthetic solution | amount of HF supplied (M/H) | 78.5 | 79.3 |
| | amount of BF$_3$ supplied (M/H) | 16.3 | 15.6 |
| | amount of aromatic aldehyde supplied (M/H) | 11.0 | 10.8 |
| | amount of unreacted aromatic hydrocarbon supplied (M/H) | 1.5 | 1.2 |
| | decomposing agent | monofluoro-benzene | monofluoro-benzene |
| | amount of decomposing agent supplied (M/H) | 40 | 36 |
| | amount of decomposing agent refluxed (M/H) in the column | 297 | 313 |
| operating conditions | pressure (ata) | 5 | 5 |
| | temperature in the decomposing column (° C) | 155 | 155 |
| gas withdrawn from the top of the column | amount of HF recovered (M/H) | 78.2 | 79.1 |
| | (recovery ratio of HF) (%) | (99.6) | (99.7) |
| | amount of BF$_3$ recovered (M/H) | 16.2 | 15.5 |
| | (recovery ratio of BF$_3$) (%) | (99.5) | (99.4) |
| | amount of decomposing agent withdrawn (M/H) | 1 | 1 |
| | amount of unreacted aromatic hydrocarbon (M/H) | 0 | 0 |
| liquid withdrawn from the bottom of the decomposing column | amount of aromatic aldehyde recovered (M/H) | 10.8 | 10.6 |
| | (recovery ratio of aromatic aldehyde) (%) | (98.0) | (98.2) |
| | amount of decomposing agent withdrawn (M/H) | 39 | 35 |
| | amount of unreacted aromatic hydrocarbon withdrawn (M/H) | 1.5 | 1.2 |
| | amount of material having high boiling point withdrawn (g/H) | 29 | 29 |

| | Object product | Example 3 p-tolu-aldehyde | Example 4 2,4-dimethyl-benzaldehyde |
|---|---|---|---|
| contents of synthetic solution | amount of HF supplied (M/H) | 82.0 | 68.6 |
| | amount of BF$_3$ supplied (M/H) | 18.4 | 13.7 |
| | amount of aromatic aldehyde supplied (M/H) | 11.8 | 10.7 |
| | amount of unreacted aromatic hydrocarbon supplied (M/H) | 1.8 | 1.7 |
| | decomposing agent | p-fluoro-toluene | p-fluoro-toluene |
| | amount of decomposing agent supplied (M/H) | 42 | 41 |
| | amount of decomposing agent refluxed (M/H) in the column | 319 | 268 |
| operating conditions | pressure (ata) | 3 | 3 |
| | temperature in the decomposing | | |

Table 1-continued

|  |  | 160 | 155 |
|---|---|---|---|
|  | column (° C) | 160 | 155 |
| gas withdrawn from the top of the column | amount of HF recovered (M/H) | 81.8 | 68.2 |
|  | (recovery ratio of HF) (%) | (99.7) | (99.4) |
|  | amount of $BF_3$ recovered (M/H) | 18.3 | 13.6 |
|  | (recovery ratio of $BF_3$) (%) | (99.6) | (99.4) |
|  | amount of decomposing agent withdrawn (M/H) | 1 | 1 |
|  | amount of unreacted aromatic hydrocarbon (M/H) | 1.5 | 0 |
| liquid withdrawn from the bottom of the decomposing column | amount of aromatic aldehyde recovered (M/H) | 11.6 | 10.4 |
|  | (recovery ratio of aromatic aldehyde) (%) | (98.5) | (97.5) |
|  | amount of decomposing agent withdrawn (M/H) | 41 | 40 |
|  | amount of unreacted aromatic hydrocarbon withdrawn (M/H) | 0.2 | 1.6 |
|  | amount of material having high boiling point withdrawn (g/H) | 30 | 35 |

|  |  | Comparative Example 1 | Comparative Example 2 | Comparative Example 3 |
|---|---|---|---|---|
|  | Object product | p-tolu-aldehyde | p-tolu-aldehyde | 2,4-dimethyl-benz-aldehyde |
| contents of synthetic solution | amount of HF supplied (M/H) | 77.3 | 80.7 | 82.3 |
|  | amount of $BF_3$ supplied (M/H) | 13.3 | 15.5 | 16.4 |
|  | amount of aromatic aldehyde supplied (M/H) | 10.2 | 11.5 | 12.8 |
|  | amount of unreacted aromatic hydrocarbon supplied (M/H) | 1.2 | 1.8 | 2.0 |
|  | decomposing agent | toluene | toluene | monochloro-benzene |
| amount of decomposing agent supplied (M/H) | | 41 | 50 | 49 |
| amount of decomposing agent refluxed (M/H) in the column | | 286 | 310 | 321 |
| operating conditions | pressure (ata) | 3 | 5 | 2 |
|  | temperature in the decomposing column (° C) | 156 | 182 | 161 |
| gas withdrawn from the top of the column | amount of HF recovered (M/H) | 75.4 | 78.0 | 79.0 |
|  | (recovery ratio of HF) (%) | (97.5) | (96.6) | (96.0) |
|  | amount of $BF_3$ recovered (M/H) | 12.9 | 14.9 | 15.7 |
|  | (recovery ratio of $BF_3$) (%) | (97.0) | (96.2) | (95.8) |
|  | amount of decomposing agent withdrawn (M/H) | 1 | 0 | 0 |
|  | amount of unreacted aromatic hydrocarbon (M/H) | — | — | 0 |
| liquid withdrawn from the bottom of the decomposing column | amount of aromatic aldehyde recovered (M/H) | 9.4 | 10.4 | 11.9 |
|  | (recovery ratio of aromatic aldehyde) (%) | (95.1) | (90.4) | (93.0) |
|  | amount of decomposing agent withdrawn (M/H) | 38 | 47 | 49 |
|  | amount of unreacted aromatic hydrocarbon withdrawn (M/H) | — | — | 1.9 |
|  | amount of material having high boiling point withdrawn (g/H) | 137 | 276 | 140 |

What we claim is:

1. A process for decomposing an aromatic aldehyde-hydrogen fluoride-boron trifluoride complex to obtain an aromatic aldehyde, hydrogen fluoride and boron trifluoride separately, characterized by carrying out the decomposition in the presence of a decomposing agent represented by the formula

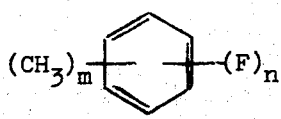

wherein $n$ is integer of from 1 to 6, inclusive, and $m$ is integer of from 0 to 5, inclusive, and a total of $n$ and $m$ is 6 or less.

2. The process defined in claim 1, characterized by carrying out the decomposition in the presence of mono-fluorobenzene.

3. The process defined in claim 1, characterized by carrying out the decomposition in the presence of a mono-fluorotoluene.

4. The process defined in claim 3, characterized by carrying out the decomposition in the presence of p-fluorotoluene.

5. The process defined in claim 1 wherein the decomposition is carried out at a temperature of from 100° C to 200° C.

6. The process defined in claim 1 wherein the decomposition is carried out at a pressure of from 2 ata to 6 ata.

7. The process defined in claim 1 wherein from 15 mols to 40 mols of the decomposing agent is refluxed in the decomposing system per 1 mol of the aromatic aldehyde supplied in the column.

* * * * *